United States Patent
Ryan

(10) Patent No.: US 7,854,736 B2
(45) Date of Patent: *Dec. 21, 2010

(54) SURGICAL INSTRUMENT AND METHOD

(75) Inventor: Phillip Andrew Ryan, Memphis, TN (US)

(73) Assignee: Gyrus Ent, L.L.C., Bartlett, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/656,096

(22) Filed: Jan. 15, 2010

(65) Prior Publication Data

US 2010/0121321 A1   May 13, 2010

Related U.S. Application Data

(63) Continuation of application No. 11/353,013, filed on Feb. 14, 2006, now Pat. No. 7,674,263.

(60) Provisional application No. 60/658,146, filed on Mar. 4, 2005.

(51) Int. Cl.
*A61B 18/14* (2006.01)

(52) U.S. Cl. .............. 606/50; 606/51; 606/180; 606/46

(58) Field of Classification Search ............. 606/41–45, 606/50, 167, 169, 170, 171, 176, 178, 179
See application file for complete search history.

(56) References Cited

U.S. PATENT DOCUMENTS

| 5,364,395 | A | 11/1994 | West, Jr. |
| 5,423,844 | A | 6/1995 | Miller |
| 5,904,681 | A | 5/1999 | West, Jr. |
| 5,941,876 | A | 8/1999 | Nardella et al. |
| 6,032,673 | A | 3/2000 | Savage et al. |
| 6,193,715 | B1 * | 2/2001 | Wrublewski et al. .......... 606/45 |
| 6,610,059 | B1 | 8/2003 | West, Jr. |
| 6,663,628 | B2 | 12/2003 | Peters |
| 6,827,725 | B2 | 12/2004 | Batchelor et al. |

(Continued)

FOREIGN PATENT DOCUMENTS

WO   WO 03/068095 A1   8/2003

*Primary Examiner*—Linda C Dvorak
*Assistant Examiner*—Amanda Scott
(74) *Attorney, Agent, or Firm*—Oliff & Berridge, PLC

(57) ABSTRACT

A surgical instrument comprises a hollow tube (18) having a cutting window (16) at the distal end portion. An inner tube (15) is disposed within the tube (18) and is mounted for rotation about its longitudinal axis. A cutting tool (17) is located at the distal end of the tube (15), and is positioned adjacent to the cutting window (16). An outer tube (14) is provided over the tube (18). A motor (5) is provided for rotating the inner tube (15), and saline is fed to the cutting window (16) via a passageway (25) between the tubes (15) and (18). The inner tube (15) has a central lumen (24) through which tissue cut by the cutting tool (17) is removed under the action of a source of suction (12). The outer surface of the tube 18 is covered with an electrically insulating layer (22) and coagulating RF signals are supplied between the tube (18) and the outer tube (14) so as to coagulate tissue at the cutting window (16). Additional apertures (40, 42; 43, 45) in the outer tube (14) and the insulating layer (22) are aligned such that a portion of the hollow tube (18) is exposed other than in the area of the cutting window (16).

7 Claims, 6 Drawing Sheets

U.S. PATENT DOCUMENTS 7,052,494 B2  5/2006  Goble et al.
7,150,747 B1  12/2006  McDonald et al.

2003/0060862 A1 *  3/2003  Goble et al. .................. 607/96

* cited by examiner

SURGICAL INSTRUMENT AND METHOD

This is a Continuation of application Ser. No. 11/353,013, filed Feb. 14, 2006, which claims priority from U.S. provisional application 60/658,146 filed Mar. 4, 2005. The entire disclosure of the prior applications are hereby incorporated by reference in their entirety.

This invention relates to a surgical instrument, and to a system and method for removing tissue from a surgical site on or within a patient's body. In a preferred construction, the invention relates to an electrosurgical system and method that can use electrical and mechanical energy to treat tissue.

Known mechanical surgical instruments include simple scalpels which are used for cutting soft tissue, rotatable shavers which are also used for removing soft tissue, and rotatable burrs which are used for cutting harder tissue such as bone.

Known electrosurgical instruments include monopolar and bipolar devices, both of which are used primarily for treating or cauterising soft tissue. Typically tissue is removed using a mechanical cutting device such as a shaver (or by an electrosurgical device operating in cutting or vaporisation mode), and then the cauterising device is used to coagulate tissue in order to stench bleeding.

It is known to use a surgical instrument which includes a mechanical element, such as a rotary shaver or burr, and an electrosurgical instrument such as a monopolar or bipolar device. A known instrument of this type is described in U.S. Pat. No. 5,904,681, which describes an instrument having a shaver or burr rotatably mounted within an outer sleeve, and an electrosurgical electrode mounted at the end of the outer sleeve on the "back" of the instrument (i.e. opposite to the cutting window of the device).

U.S. Pat. No. 6,610,059 is a further device from the same inventor in which an electrosurgical electrode is provided on the back of a mechanical cutting device. Another prior art device is U.S. Pat. No. 6,193,715 which provides an adapter for converting a conventional mechanical cutting device such as a shaver or burr into a combined mechanical/electrosurgical instrument.

It is an object of the present invention to provide an improved surgical device, bearing in mind the limitations of the prior art devices described above.

Accordingly, there is provided a blade assembly for a surgical instrument comprising a) an intermediate hollow tube having a central passageway and a cutting window at a distal end thereof;
b) an inner hollow tube rotatably mounted in the central passageway of the intermediate tube and providing a central suction lumen;
c) a cutting tool disposed at the distal end of the inner tube such that the cutting tool is accessible through the cutting window of the intermediate tube, the cutting tool including a cut-out defining a tissue-cutting edge;
d) an outer tube disposed over the intermediate hollow tube and having an opening at its distal end so as to allow access to the cutting window of the intermediate tube;
e) an electrically insulating layer disposed between the intermediate and outer tubes, the intermediate and outer tubes both being electrically conducting; and
f) first and second contacts associated with the outer and intermediate tubes respectively for connecting the tubes to respective poles of an electrosurgical generator;

the arrangement being such that the rotation of the cutting tool is capable of causing the cutting of tissue in the region of the cutting window, while the intermediate and outer tubes form the electrodes of a bipolar electrosurgical instrument capable of coagulating tissue in the region of the cutting window, there being additionally provided apertures in both the outer tube and the insulating layer, the apertures being aligned such that a portion of the intermediate tube at the distal end is exposed other than in the region of the cutting window.

It will be appreciated that the electrosurgical action of the present instrument is primarily in the region of the cutting window, as opposed to the reverse side of the instrument as in U.S. Pat. Nos. 5,904,681 and 6,610,059. This means that an electrosurgical coagulating signal can be applied to tissue simultaneously with the mechanical cutting, without having to re-orient the instrument. The electrosurgical coagulating signal is applied directly in the same region as the cutting action, i.e. in the proximity of the cutting window. However, the provision of the additional apertures in the outer tube and insulating layer allows for an additional area of electrosurgical action, in an area other than that of the cutting window.

The electrically insulating layer is conveniently provided between the intermediate tube and the outer tube. In a preferred embodiment, the insulating layer is provided by means of an insulating material deposited on to the outer surface of the intermediate layer. Alternatively, the insulating material can be deposited on to the inner surface of the outer tube. The insulating material is conveniently a non-conductive polymer such as P.T.F.E. silicone rubber, or Ethylene Chloro-trifluoroethylene (ECTFE).

According to a preferred embodiment, the apertures in the outer tube and the insulating layer comprise a slot starting at the cutting window and extending therefrom. Conveniently, the slot extends from the cutting window along the distal tip of the blade, and extends to the reverse of the outer tube opposite the cutting window. This provides the user of the instrument with the options of simultaneously cutting and coagulating tissue at the cutting window, as well as coagulation using the tip of the instrument or the portion of the instrument opposite the cutting window. Thus, in the event that bleeding occurs despite the simultaneous coagulation at the cutting window, the tip or reverse of the instrument can be used as a "spot coagulation" tool.

In an alternative embodiment, the apertures in the outer tube and the insulating layer comprise a discrete portion on the distal tip of the blade. This discrete portion may alternatively be on the reverse of the outer tube opposite the cutting window, or both in combination (extending from the distal tip of the blade to the reverse of the outer tube opposite the cutting window). With any of the above arrangements, the tool allows for spot coagulation in addition to the simultaneous cutting and coagulation provided at the cutting window.

According to a further aspect of the invention, there is provided a surgical system including i) a blade assembly comprising;
   a) an intermediate hollow tube having a central passageway and a cutting window at a distal end thereof;
   b) an inner hollow tube rotatably mounted in the central passageway of the intermediate tube and providing a central suction lumen;
   c) a cutting tool disposed at the distal end of the inner tube such that the cutting tool is accessible through the cutting window of the intermediate tube, the cutting tool including a cut-out defining a tissue-cutting edge;
   d) an outer tube disposed over the intermediate hollow tube and having an opening at its distal end so as to allow access to the cutting window of the intermediate tube;

e) an electrically insulating layer disposed between the intermediate and outer tubes, the intermediate and outer tubes both being electrically conducting; and f) first and second contacts associated with the outer and intermediate tubes respectively for connecting the tubes to respective poles of an electrosurgical generator;

ii) a motor adapted to rotate the inner hollow tube within the intermediate tube;

iii) a source of suction connected to the central suction lumen of the inner hollow tube; and iv) an electrosurgical generator connected to the first and second contacts so as to selectively supply RF energy between the intermediate and outer tubes;

the arrangement being such that the rotation of the cutting tool is capable of causing the cutting of tissue in the region of the cutting window, while the RF energy supplied to the intermediate and outer tubes coagulates tissue in the region of the cutting window, and there is additionally provided apertures in both the outer tube and the insulating layer, the apertures being aligned such that a portion of the intermediate tube at the distal end is exposed other than in the region of the cutting window.

In a preferred embodiment, there is also provided a source of irrigating fluid, adapted to irrigate the blade assembly. The irrigating fluid is preferably an electrically conductive fluid such as saline, and is conveniently transmitted to the cutting tool between the inner tube and the intermediate tube. The irrigating fluid not only helps to cool and clean the cutting tool, but also assists in the electrosurgical coagulation process.

According to a further aspect of the invention, there is provided a method of surgically removing tissue from a surgical site on or in the body of a patient, the method comprising the steps of i) introducing to the surgical site a surgical instrument including
   a) an intermediate hollow tube having a central passageway and a cutting window at a distal end thereof;
   b) an inner hollow tube rotatably mounted in the central passageway of the intermediate tube and providing a central suction lumen;
   c) a cutting tool disposed at the distal end of the inner tube such that the cutting tool is accessible through the cutting window of the intermediate tube, the cutting tool including a cut-out defining a tissue-cutting edge;
   d) an outer tube disposed over the intermediate hollow tube and having a first opening at its distal end so as to allow access to the cutting window of the intermediate tube, and a second opening remote from the cutting window; and
   e) an electrically insulating layer disposed between the intermediate and outer tubes, the intermediate and outer tubes both being electrically conducting, the electrically insulating layer having an aperture in alignment with the second opening in the outer tube;

ii) rotating the inner hollow tube such as to cause the cutting tool to rotate adjacent the cutting window;

iii) applying suction to the suction lumen of the inner tube so as to cause tissue to be drawn into the cutting window and contacted by the rotating cutting tool;

iv) supplying RF energy between the intermediate and outer tubes such that tissue coming into contact therewith is coagulated;

v) manipulating the surgical instrument so as to cut and coagulate tissue at the in the region of the cutting window; and vi) manipulating the surgical instrument so as to coagulate tissue in the region of the second opening in the outer tube.

The invention will now be described in greater detail, by way of example, with reference to the drawings, in which:—

Figure 1:
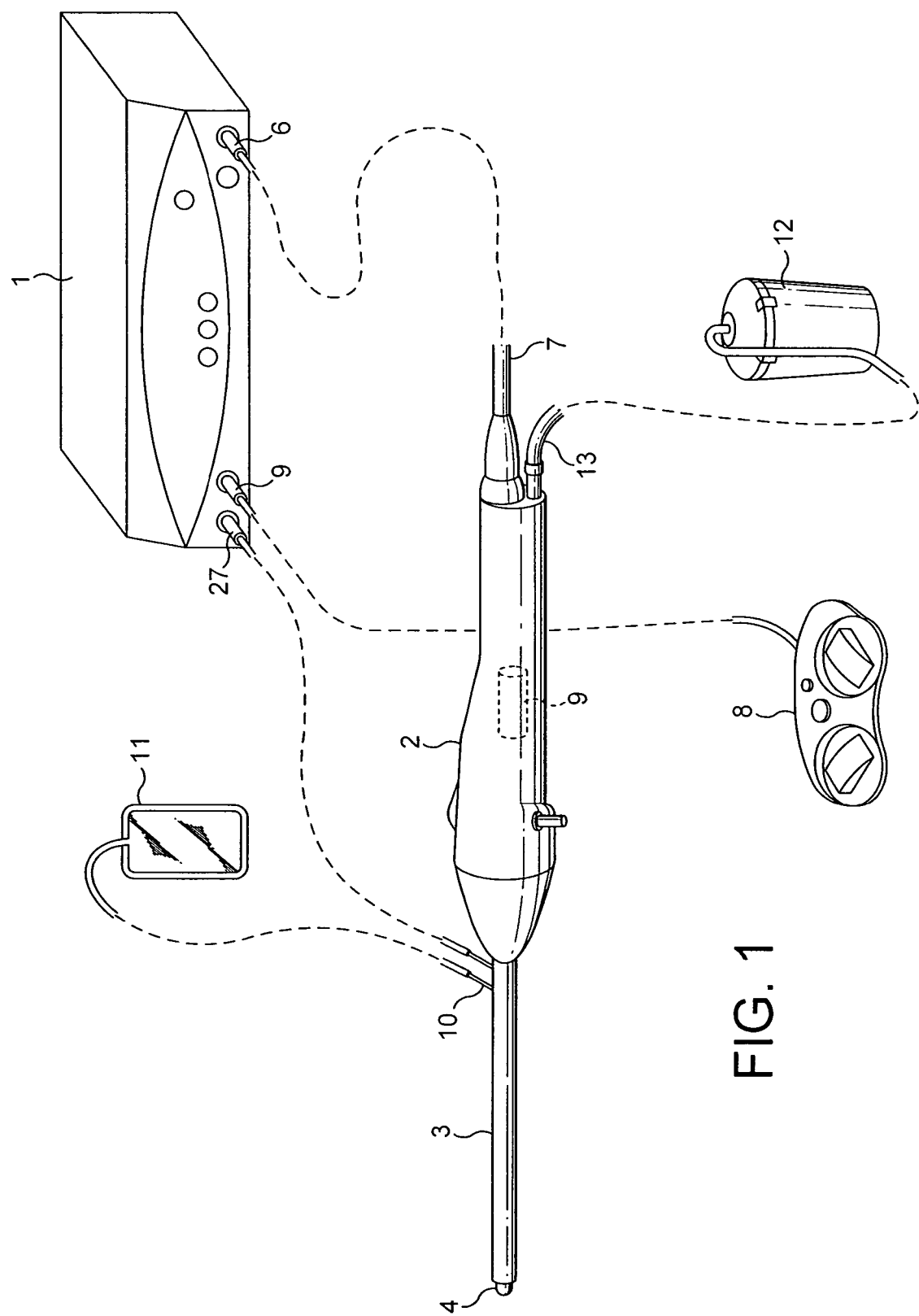
FIG. 1 is a schematic diagram of a surgical system incorporating a surgical instrument in accordance with the invention.

Referring to the drawings, FIG. 1 shows a surgical system which includes a controller/generator 1 and a handpiece 2 having a detachable surgical probe shown generally at 3. The probe 3 includes a rotatable inner tubular member 15, driven by a motor shown schematically at 5 within the handpiece. Power signals for the motor 5 are supplied to the handpiece 2 from an output socket 6 on the generator 1, via connector cord 7. Activation of the controller 1 may be performed by means of footswitch 8, coupled to the controller by means of connector cord 9. An inlet port 10 allows saline to be fed from a saline source 11 to the distal end of the probe 3. A source of suction 12 is also provided, coupled to the handpiece by cord 13. Cord 27 supplies electrosurgical coagulation signals from the generator 1 to the probe 3.

Figure 2:
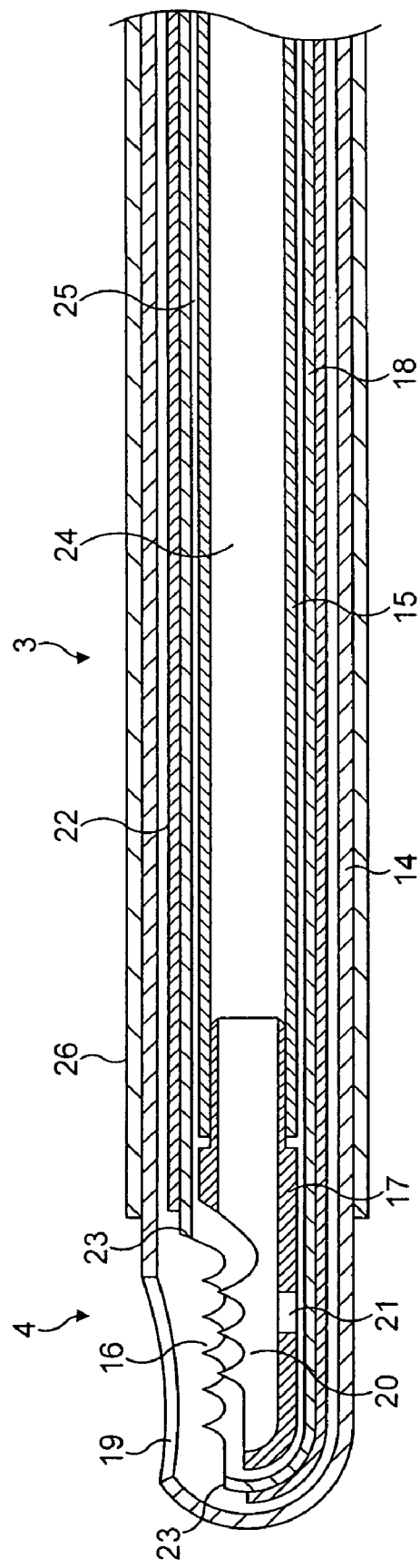
FIG. 2 is a sectional side view of the distal end of the surgical instrument of FIG. 1.

FIG. 2 shows a sectional view of the distal end 4 of the probe 3. The probe 3 comprises an inner tubular member 15, an outer tubular member 14 and an intermediate tubular member 18. A cutting tool 17 is located at the distal end of the inner member 15, and can be accessed through lateral cutting windows 16 and 19 in the intermediate and outer tubular members respectively. The cutting tool includes a cut-out portion 20 having a periphery constituted by a serrated edge, and an optional suction aperture 21 located opposite the cut-out portion 20.

The tubes 14, and 18 are both formed of a conductive metallic material such as stainless steel, although the outer tubular member 14 can alternatively be formed of copper (which is better at conducting heat away from the distal end 4 of the probe 3). The intermediate tubular member 18 is coated with an electrically insulating Ethylene Chloro-trifluoroethylene (ECTFE) layer 22, the layer 22 stopping marginally short of the distal end of the tube 18 so as to leave exposed portions as shown at 23. Both the insulating layer 22 and the outer tubular member 14 are provided with additional apertures, as will be described in more detail later.

The inner tubular member 15 is formed of a non-conducting flexible polymer material, with the cutting tool 17 being formed of stainless steel. (Alternatively, the inner tube 15 can be formed of stainless steel in which case the cutting tool 17 can be formed integrally with the inner tube 15.) The inner tubular member 15 is hollow defining a suction lumen 24, which in use is connected to the source of suction 12. A passageway 25 between the inner tubular member 15 and the intermediate member 18 is connected in use to the saline source 11, and is used to deliver saline to the distal end 4 of the probe 3. The outer member 14 is optionally covered with a heat-shrink electrically insulating sleeve 26, covering the probe 3 with the exception of the distal end 4 including the cutting window 19.

Figure 3:
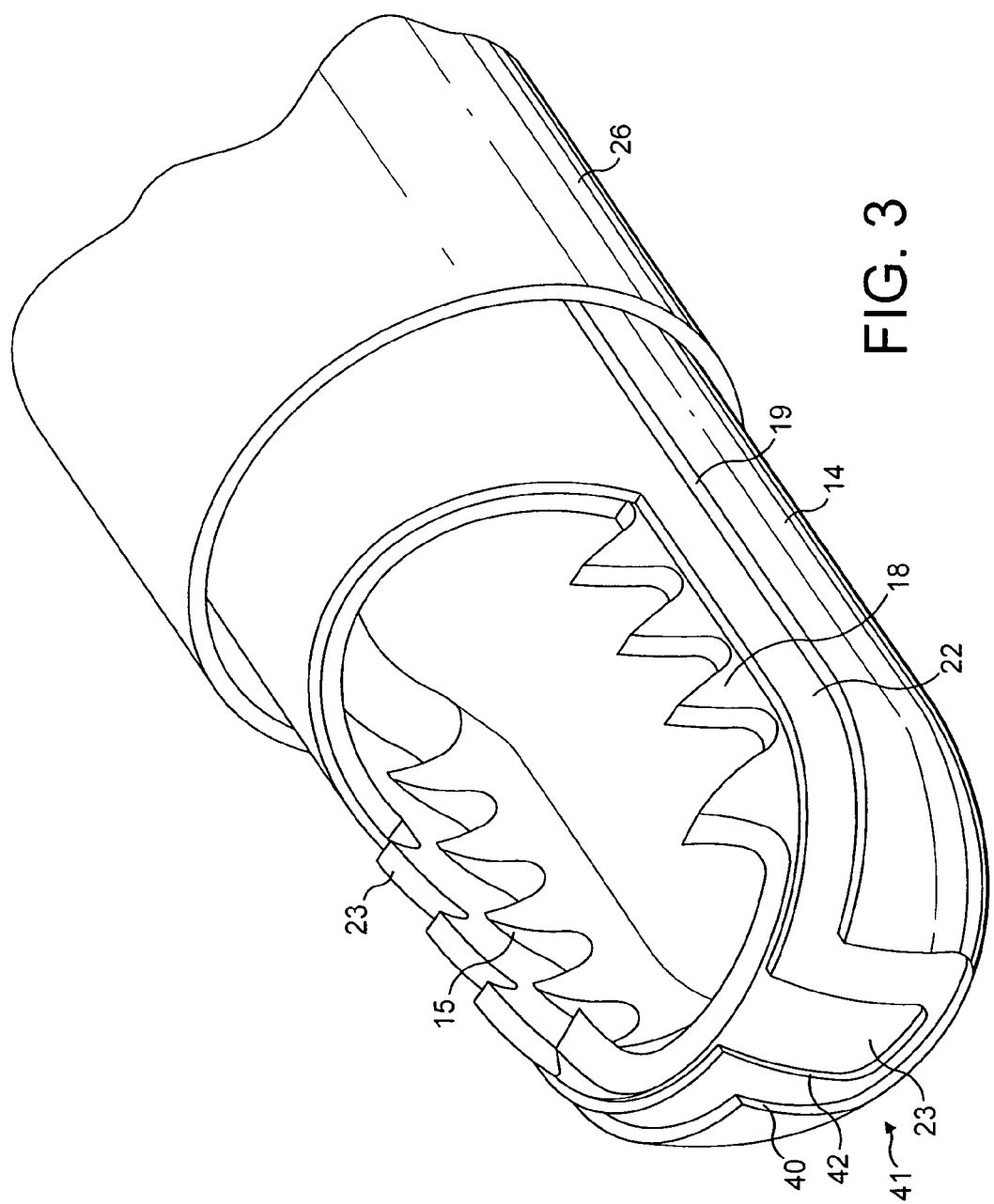
FIG. 3 is a schematic close-up view of one embodiment of the distal end of the probe of the instrument of FIG. 1.

FIG. 3 shows a first embodiment of the distal end of the instrument in which the inner tubular member 15, outer tubular member 14, and intermediate tubular member 18 are shown as previously described. The insulating layer 22 on the intermediate member 18 is also shown. A first slot 40 is present in the outer member 14, the slot extending from the window 19 along the distal-most tip 41 of the probe 3, and ending at the bottom of the distal tip 41. A similar slot 42 is present in the insulating layer 22, the slot 42 being generally in alignment with the slot 40 such that the intermediate member 18 is visible through the slots 40 and 42.

Figure 4:
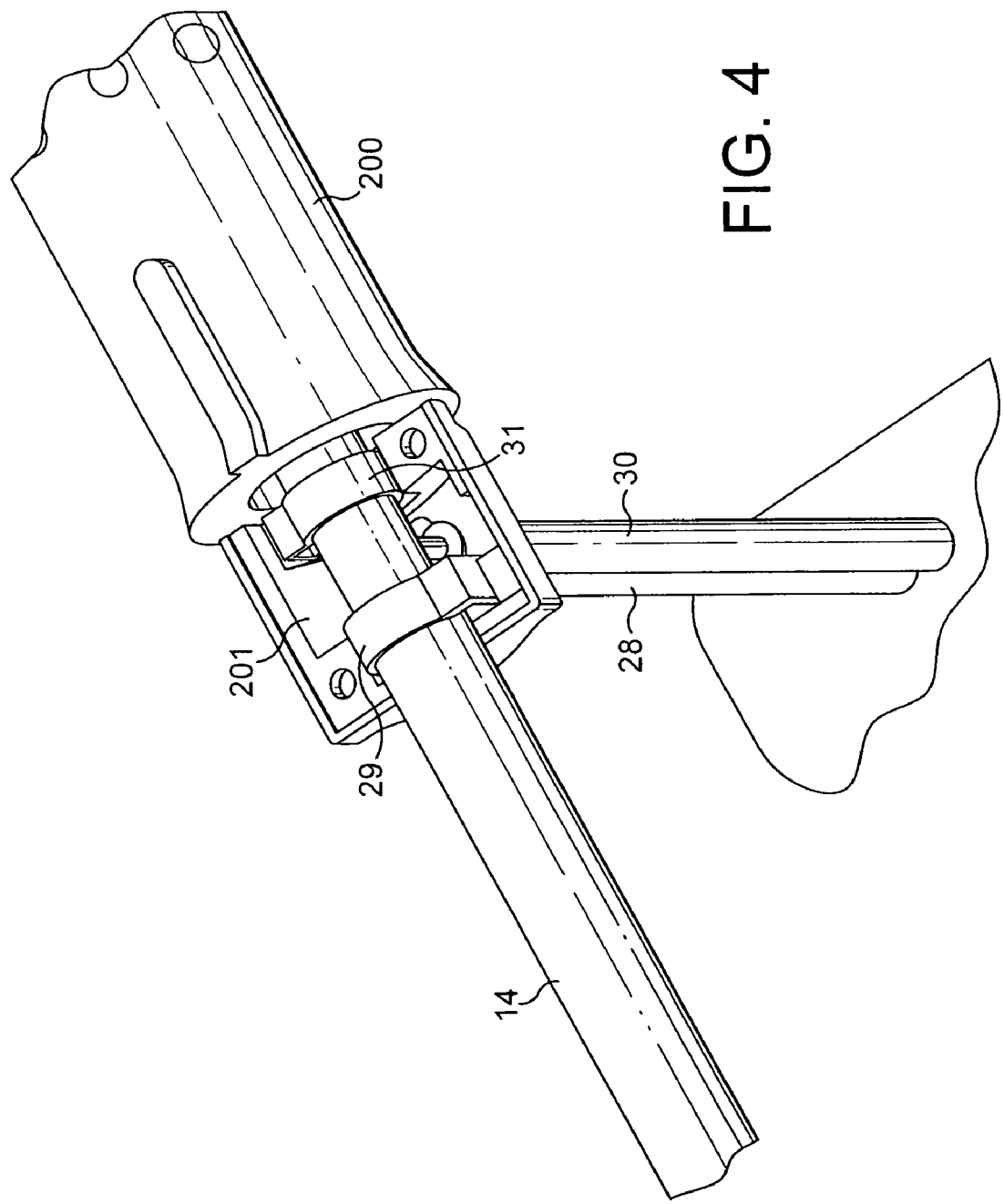
FIG. 4 is a schematic view, shown partly in section, of the proximal end of the probe of the surgical instrument of FIG. 1.

FIG. 4 shows how the intermediate tubular member 18 and the outer member 14 are connected to the electrosurgical generator 1. A first lead 28 supplies signals from one pole of the generator 1, and is connected to the outer tubular member 14 by means of clip assembly 29. A second lead 30 is connected to the other pole of the generator 1, and is in electrical communication with the intermediate tubular member 18 by means of second clip assembly 31. The clip assemblies are covered by a plastics casing 201, which is filled with epoxy potting compound to separate the first and second clip assemblies 29 and 31.

The use of the instrument will now be described. In use, when the cutting of tissue is required, the motor 5 is activated to rotate the inner tubular member 15, thereby causing the corresponding rotation of the cutting tool 17. The probe 3 is moved to engage tissue to be excised, and the tissue is drawn through the cutting windows 16 and 19 by the suction applied through the suction lumen 24 in the inner member 15. When the tissue enters the cutting window 16, it is severed by the rotation of the cutting tool 17 and the excised tissue is evacuated by the suction along the suction lumen 24.

When the coagulation of tissue is required, the electrosurgical generator 1 is actuated to supply bipolar coagulation signals to the intermediate tube 18 and outer tube 14, via the clip assemblies 29 and 31. Tissue coming into contact with the exposed portions 23 of the intermediate tube 18 will be coagulated by the electrosurgical signals from the generator 1. The exposed portions of the intermediate tube 18 firstly include the area around the cutting window 16, electrosurgical current flowing between the intermediate tubular member 18 and the outer member 14. Saline fed to the distal end of the probe from saline source 11 helps to carry the current between the members 18 and 14. The exposed portions of the intermediate tube 18 secondly include the area around the slots 40 and 42. This allows coagulation of tissue at the distal tip of the probe 3, and also on the reverse face opposite the window 19. This allows the user to perform coagulation of tissue (for example to stem the flow of blood from bleeding tissue), without the user needing to stop the rotation of the cutting tool 17, by using areas of the instrument remote from the cutting window thereof.

Figure 5:
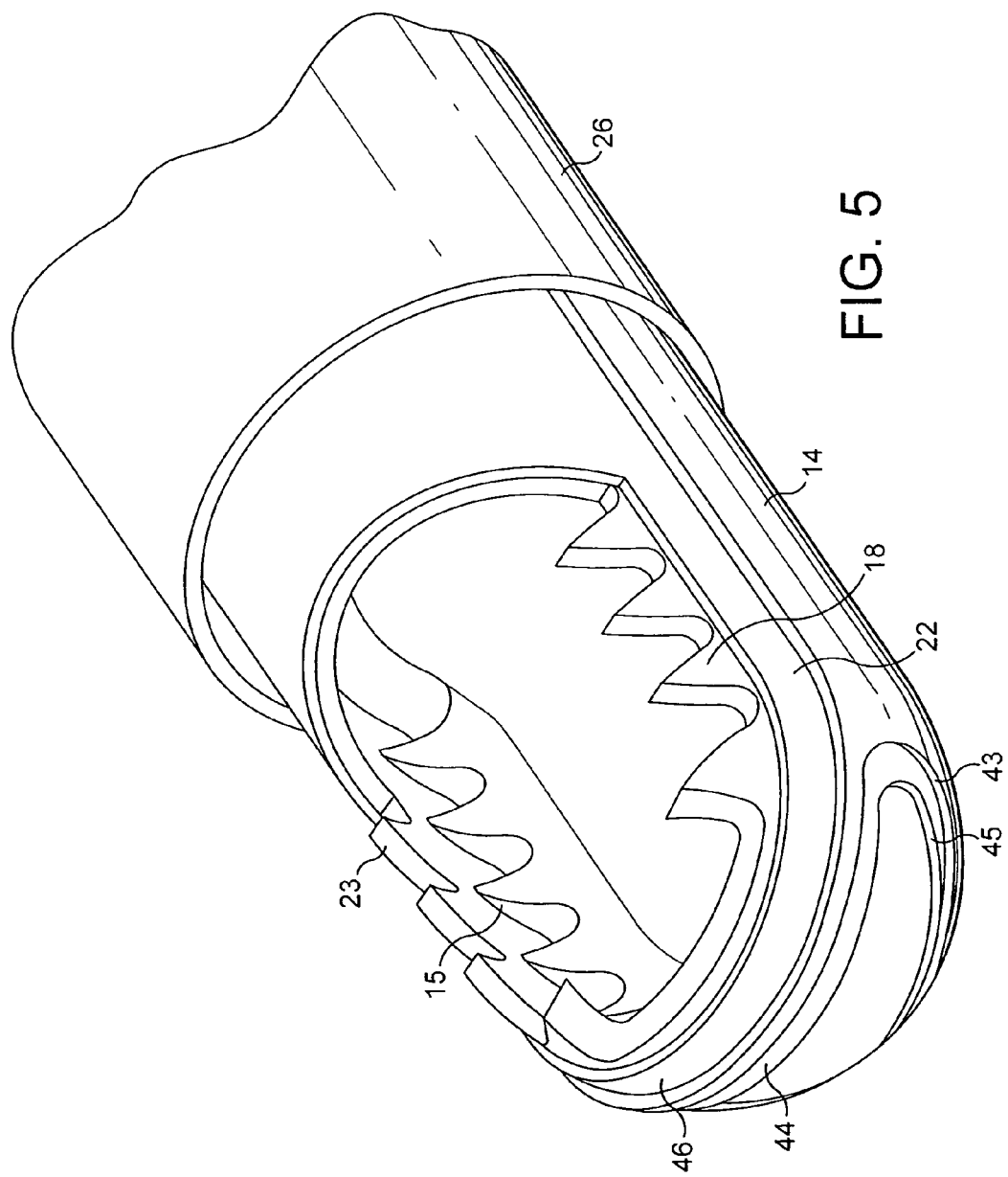
FIG. 5 is a schematic close-up view of an alternative embodiment of the distal end of the probe of the instrument of FIG. 1.

FIG. 5 shows an alternative embodiment of instrument in which the additional apertures are formed not by slots but by discrete apertures in the outer member 14 and insulating layer 22. An aperture 43 in the outer member extends around the distal-most tip 41 of the probe, with a bar 44 of material separating the aperture from the window 19. A similar aperture 45 is present in the layer 22, in alignment with the aperture 43 and having a broader bar 46 underlying the bar 44 of material provided by the outer member 14. The operation of the instrument is as previously described, with the portion of the intermediate member 18 exposed through the apertures 43 and 45 being available for the coagulation of tissue in an area remote from the cutting tool 17.

Figure 6:
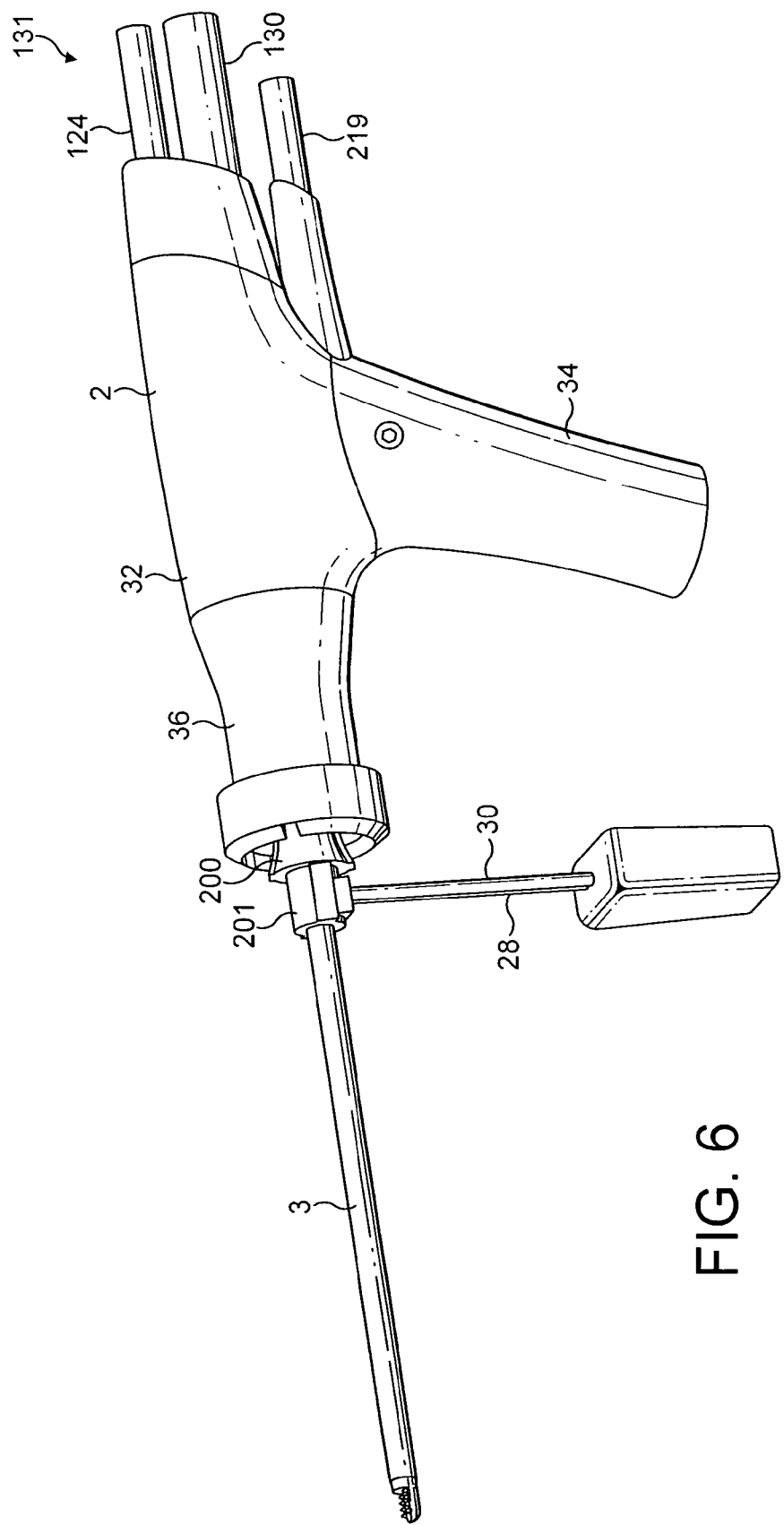
FIG. 6 is a side view of a surgical instrument in accordance with an alternative embodiment of the invention.

FIG. 6 shows an alternative embodiment of surgical device in which the handpiece 2 includes an upper portion 32 and a lower portion 34 defining a pistol grip arrangement. The upper portion 32 extends generally parallel to the probe 3, while the lower portion 34 extends at an angle thereto. The probe 3 is attached to the upper portion of the handpiece 2 by means of a hub 200 and collet assembly 36. The motor 5 (not shown in FIG. 4) is located in the lower portion 34 of the handpiece, and is controlled by signals via control line 219. Fluid irrigation and suction are provided to the handpiece 2 via dual tubing 131, the fluid supply being via tube 124 and the suction supply via tube 130. The dual tubing 131 is attached to the handpiece 2 by means of a connector 112.

The swivel collet assembly 36 is provided at the front end of the upper portion 32 of the handle 2. Disposing the collet assembly 36 at this location enables an operator, such as a surgeon, holding the handle 2 in a pistol grip manner, to touch and rotate the assembly collet 36 or a portion thereof with the tip of at least one of the surgeon's fingers. Rotating at least a portion of the collet assembly 36 in this manner enables the cutting window of the probe 3 to rotate, thereby orienting the direction of the shaving and/or cutting of the desired bodily material. The RF leads 28 and 30 and the plastics casing 201 are shown at the proximal end of the probe 3.

It will be appreciated by those skilled in the art that the embodiments described above firstly provide both mechanical cutting of tissue and electrosurgical coagulation at substantially the same part of the instrument, thereby avoiding the need for the surgeon to move or otherwise reorient the instrument to change between cutting and coagulation. However, there is also provided the option for tissue coagulation at a portion of the instrument remote from the cutting window, to allow the user to be able to coagulate tissue without stopping the rotation of the cutting element.

The invention claimed is:

1. A blade assembly for a surgical instrument usable with an electrosurgical generator, the blade assembly being usable to cut tissue and comprising:
   a) an electrically conductive, hollow intermediate tube having a distal end, a tip at the distal end, a central passageway and a cutting window at the distal end;
   b) a hollow inner tube rotatably mounted in the central passageway of the intermediate tube and providing a central suction lumen, the inner tube defining a distal end;
   c) a cutting tool disposed at the distal end of the inner tube that is accessible to the tissue through the cutting window of the intermediate tube, the cutting tool including a cut-out defining a tissue-cutting edge;
   d) an electrically conductive outer tube disposed over the intermediate hollow tube, the outer tube having a distal end and an opening at the distal end of the outer tube, the opening being radially aligned with the cutting window of the intermediate tube, the outer tube also defining a slot extending across a tip of the distal end;
   e) an electrically insulating layer disposed between the intermediate and outer tubes, the insulating layer defining a distal end and a slot extending across a tip of the distal end; and
   f) first and second contacts associated with the outer and intermediate tubes respectively, which connect the outer and intermediate tubes to respective poles of the electrosurgical generator;

wherein the rotation of the cutting tool cuts tissue adjacent to the cutting window of the intermediate tube, while the intermediate and outer tubes form electrodes of a bipolar electrosurgical instrument capable of coagulating the tissue adjacent to the cutting window of the intermediate tube, the slots of the outer tube and the insulating layer being aligned such that the distal tip of the intermediate tube is exposed through the slots of the outer tube and the insulating layer to the tissue and is capable of coagulating tissue at the distal tip of the intermediate tube.

2. A blade assembly according to claim 1 wherein the electrically insulating layer is an insulating material on the outer surface of the intermediate tube.

3. A blade assembly according to claim 1 wherein the slots in the outer tube and the insulating layer extend from the cutting window of the intermediate tube.

4. A blade assembly according to claim 3 wherein the slot in the outer tube extends from the cutting window of the intermediate tube along a distal tip of the blade assembly to the reverse of the outer tube opposite the cutting window of the outer tube.

5. A blade assembly according to claim 1 wherein the slots in the outer tube and the insulating layer comprise a discrete portion on the distal tip of the blade assembly.

6. A method of surgically removing tissue from a surgical site on or in the body of a patient, the method comprising the steps of
   i) introducing to the surgical site a surgical instrument including
      a) an electrically conductive intermediate hollow tube having a central passageway and a cutting window at a distal end thereof;
      b) an inner hollow tube rotatably mounted in the central passageway of the intermediate tube and providing a central suction lumen;
      c) a cutting tool disposed at a distal end of the inner tube such that the cutting tool is accessible through the cutting window of the intermediate tube, the cutting tool including a cut-out defining a tissue-cutting edge;
      d) an electrically conductive outer tube disposed over the intermediate hollow tube and defining a first opening at a distal end of the outer tube that is radially aligned with the cutting window of the intermediate tube, and a first slot that extends from the cutting window across a distal tip of the outer tube; and
      e) an electrically insulating layer disposed between the intermediate and outer tubes, the electrically insulating layer defining a second slot in alignment with the first slot in the outer tube;
   ii) rotating the inner hollow tube such as to cause the cutting tool to rotate adjacent the cutting window;
   iii) applying suction to the suction lumen of the inner tube so as to cause tissue to be drawn into the cutting window and contacted by the rotating cutting tool;
   iv) supplying RF energy between the intermediate and outer tubes such that tissue coming into contact therewith is coagulated;
   v) manipulating the surgical instrument so as to cut and coagulate tissue in the region of the cutting window; and
   vi) manipulating the surgical instrument so as to coagulate tissue in the region of the first slot in the outer tube.

7. A blade assembly for use with a surgical instrument and an electrosurgical generator, the blade assembly configured to coagulate tissue at a cutting window and at a distal tip of the blade assembly, the blade assembly comprising:
   a) an electrically conductive outer tube including a distal end that defines a first opening aligned with the cutting window and defines a first slot aligned with the distal tip of the blade assembly;
   b) an electrically conductive intermediate hollow tube defining a central passageway and a distal end, the distal end of the intermediate tube defining a first opening that is aligned with the cutting window, the intermediate tube extending coaxially within the outer tube;
   c) first and second electrical contacts associated with the outer and intermediate tubes respectively, the first and second electrical contacts being electrically connected to respective poles of the electrosurgical generator;
   d) an electrically insulating layer disposed between the intermediate and outer tubes, the insulating layer defining a first opening that is aligned with the cutting window and a first slot that is aligned with the distal tip of the blade assembly;
   e) an inner hollow tube rotatably mounted coaxially within the intermediate tube, the inner tube providing a suction lumen; and
   f) a cutting tool disposed at a distal end of the inner tube and accessible to the tissue through the cutting window, the cutting tool defining a cutting edge;
   wherein rotation of the inner tube cuts tissue in the region of the cutting window, and the application of RF energy from the electrosurgical generator to the first and second contacts coagulates tissue at the cutting window and at the distal tip of the blade assembly.

* * * * *

UNITED STATES PATENT AND TRADEMARK OFFICE
CERTIFICATE OF CORRECTION

PATENT NO. : 7,854,736 B2
APPLICATION NO. : 12/656096
DATED : December 21, 2010
INVENTOR(S) : Phillip Ryan Page 1 of 1

It is certified that error appears in the above-identified patent and that said Letters Patent is hereby corrected as shown below:

On the Title Page,

Please delete the following:

"(73)    Assignee:    Gyrus Ent, L.L.C., Bartlett, TN (US)

And Replace with:

(73)    Assignee:    Gyrus ENT, L.L.C., Bartlett, TN (US)

Signed and Sealed this
Fourteenth Day of June, 2011

David J. Kappos
*Director of the United States Patent and Trademark Office*